United States Patent
Cottard et al.

(10) Patent No.: US 7,651,539 B2
(45) Date of Patent: Jan. 26, 2010

(54) DYE COMPOSITION OF ACIDIC PH COMPRISING 2,3-DIAMINO-6,7-DIHYDRO-1H,5H-PYRAZOLO[1,2-A]PYRAZOL-1-ONE, A COUPLER, A PARTICULAR SURFACTANT AND AN OXIDIZING AGENT AND PROCESSES AND KITS USING SAID COMPOSITION

(75) Inventors: François Cottard, Courbevoie (FR); Florence Laurent, Bois Colombes (FR); Delphine Allard, Westfield, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/987,450

(22) Filed: Nov. 30, 2007

(65) Prior Publication Data

US 2008/0163883 A1    Jul. 10, 2008

Related U.S. Application Data

(60) Provisional application No. 60/874,271, filed on Dec. 12, 2006.

(30) Foreign Application Priority Data

Nov. 30, 2006    (FR) .................................. 06 55213

(51) Int. Cl.
*A61Q 5/10* (2006.01)
*C07D 231/44* (2006.01)

(52) U.S. Cl. ........................ 8/405; 8/406; 8/407; 8/408; 8/410; 8/411; 8/412; 8/421; 8/567; 548/369.1

(58) Field of Classification Search ...................... 8/405, 8/406, 407, 408, 410, 411, 412, 421, 567; 548/369.1

See application file for complete search history.

(56) References Cited

U.S. PATENT DOCUMENTS

| 3,012,884 | A | 12/1961 | de Ramaix et al. |
|---|---|---|---|
| 4,003,699 | A | 1/1977 | Rose et al. |
| 4,128,425 | A | 12/1978 | Greenwald |
| RE30,199 | E | 1/1980 | Rose et al. |
| 4,823,985 | A | 4/1989 | Grollier et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,718,731 | A | 2/1998 | Loewe et al. |
| 5,766,576 | A | 6/1998 | Löwe et al. |
| 6,099,592 | A | 8/2000 | Vidal et al. |
| 6,099,593 | A | 8/2000 | Terranova et al. |
| 6,284,003 | B1 | 9/2001 | Rose et al. |
| 6,338,741 | B1 | 1/2002 | Vidal et al. |
| 6,436,151 | B2 * | 8/2002 | Cottard et al. .................. 8/406 |
| 6,645,258 | B2 | 11/2003 | Vidal et al. |
| 6,660,046 | B1 | 12/2003 | Terranova et al. |
| 6,730,789 | B1 | 5/2004 | Birault et al. |
| 7,285,137 | B2 | 10/2007 | Vidal et al. |
| 7,485,156 | B2 | 2/2009 | Saunier |
| 7,488,355 | B2 | 2/2009 | Saunier |
| 7,488,356 | B2 | 2/2009 | Saunier |
| 2001/0023514 | A1 | 9/2001 | Cottard et al. |
| 2002/0046431 | A1 * | 4/2002 | Laurent et al. .................. 8/405 |
| 2002/0050013 | A1 | 5/2002 | Vidal et al. |
| 2002/0088062 | A1 | 7/2002 | Pratt |
| 2003/0019051 | A9 | 1/2003 | Vidal et al. |
| 2005/0166335 | A1 * | 8/2005 | Vidal et al. .................... 8/405 |
| 2007/0006398 | A1 | 1/2007 | Hercouet |
| 2008/0005853 | A1 | 1/2008 | Cottard et al. |
| 2008/0016627 | A1 | 1/2008 | Cottard et al. |
| 2008/0016628 | A1 | 1/2008 | Cottard et al. |
| 2009/0007347 | A1 | 1/2009 | Cottard et al. |

FOREIGN PATENT DOCUMENTS

| CH | 421 343 | 9/1966 |
|---|---|---|
| DE | 1 959 009 | 12/1970 |
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| DE | 196 19 112 | 11/1997 |
| DE | 101 48 847 A1 | 5/2003 |
| EP | 0 770 375 A1 | 5/1997 |
| EP | 0 873 745 | 10/1998 |

(Continued)

OTHER PUBLICATIONS

French Search Report for FR 0655213, dated Jul. 24, 2007 (corresponding to present application).
French Search Report for FR 0652557, dated Mar. 9, 2007, (corresponding to co-pending U.S. Appl. No. 11/812,603).
French Search Report for FR 0652558, dated Mar. 13, 2007, (corresponding to co-pending U.S. Appl. No. 11/812,610).
French Search Report for FR 0652549 dated Mar. 6, 2007, (corresponding to co-pending U.S. Appl. No. 11/812,616).
French Search Report for FR 0655214 dated Mar 6, 2007, (corresponding to co-pending U.S. Appl. No. 11/987,451).

(Continued)

*Primary Examiner*—Eisa B Elhilo
(74) *Attorney, Agent, or Firm*—Finnegan, Henderson, Farabow, Garrett & Dunner, LLP

(57) ABSTRACT

Disclosed herein are compositions for dyeing keratin fibers, for example human keratin fibers such as the hair, comprising 2,3-diamino-6,7-dihydro-1H,5H-pyrazolo[1,2-a]pyrazol-1-one or an addition salt thereof, at least one oxidation base, at least one coupler, at least one surfactant chosen from oxyalkylenated or glycerolated fatty alcohols, anionic surfactants of sulfate or sulfonate type and amphoteric surfactants of betaine type, and at least one oxidizing agent, the pH of the composition ranging from 5.5 to 7.5. The compositions disclosed herein make it possible to obtain coloration on keratin fibers with tints in red, coppery or mahogany tones that are sufficiently visible on natural or dyed hair and/or uniform from the roots to the ends.

20 Claims, No Drawings

FOREIGN PATENT DOCUMENTS

| | | |
|---|---|---|
| EP | 1 250 909 | 10/2002 |
| EP | 1 550 656 A1 | 7/2005 |
| FR | 2 586 913 A1 | 3/1987 |
| FR | 2 733 749 A1 | 11/1996 |
| FR | 2 750 048 A1 | 12/1997 |
| FR | 2 801 308 A1 | 5/2001 |
| FR | 2 886 132 | 12/2006 |
| FR | 2 886 135 | 12/2006 |
| FR | 2 886 136 | 12/2006 |
| FR | 2 886 137 | 12/2006 |
| FR | 2 886 138 | 12/2006 |
| FR | 2 886 139 | 12/2006 |
| FR | 2 886 140 | 12/2006 |
| FR | 2 886 141 | 12/2006 |
| FR | 2 886 142 | 12/2006 |
| FR | 2 902 323 | 12/2007 |
| FR | 2 902 327 | 12/2007 |
| FR | 2 902 328 | 12/2007 |
| GB | 1 005 233 | 9/1965 |
| GB | 1 026 978 | 4/1966 |
| GB | 1 153 196 | 5/1969 |
| GB | 1 486 576 | 11/1974 |
| JP | 05 163 124 A | 3/1987 |
| JP | 2-019576 A | 1/1990 |
| JP | 2002-535312 | 10/2002 |
| WO | WO 94/08969 A1 | 4/1994 |
| WO | WO 94/08970 A1 | 4/1994 |
| WO | WO 96/15765 A1 | 5/1996 |

OTHER PUBLICATIONS

English language abstract of DE 101 48 847 A1, May 10, 2003.
English language abstract of EP 0 770 375 B1, May 2, 1997.
English language esp@cenet abstract of FR 2 801 308, May 25, 2001.
English language abstract of JP 2-019576, Jan. 23, 1990.
English language abstract of JP 5-163124, Jun. 29, 1993.
EP search report for EP 07121666.7 dated Apr. 2, 2008 (corresponding to co-pending U.S. Appl. No. 11/987,451).
Office Action dated Aug. 15, 2008, in co-pending U.S. Appl. No. 11/812,616.
Office Action dated Aug. 4, 2008, in co-pending U.S. Appl. No. 11/812,603.
Office Action dated Aug. 6, 2008, in co-pending U.S. Appl. No. 11/812,610.
Office Action dated Oct. 28, 2008, in co-pending U.S. Appl. No. 11/987,451.
STIC Search Report dated Jul. 13, 2008, in co-pending U.S. Appl. No. 11/812,603.
STIC Search Report dated Jul. 31, 2008, in co-pending U.S. Appl. No. 11/812,610.
Co-pending U.S. Appl. No. 10/999,999, filed Dec. 1, 2004.
Co-pending U.S. Appl. No. 11/812,603, filed Jun. 20, 2007.
Co-pending U.S. Appl. No. 11/812,610, filed Jun. 20, 2007.
Co-pending U.S. Appl. No. 11/812,616, filed Jun. 20, 2007.
Co-pending U.S. Appl. No. 11/898,438, filed Sep. 12, 2007.
Co-pending U.S. Appl. No. 11/987,451, filed Nov. 30, 2007.
English language Abstract of DE 1 959 009, dated Dec. 3, 1970.
English language Abstract of DE 196 19 112, dated Nov. 13, 1997.
English language Abstract of EP 0 873 745, dated Oct. 28, 1998.
English language Abstract of EP 1 250 909, dated Oct. 23, 2002.
English language Abstract of FR 2 886 135, dated Dec. 1, 2006.
English language Abstract of FR 2 886 136, dated Dec. 1, 2006.
English language Abstract of FR 2 886 140, dated Dec. 1, 2006.
English language Abstract of FR 2 886 141, dated Dec. 1, 2006.
English language Abstract of FR 2 886 142, dated Dec. 1, 2006.
Helvetica Chimica Acta., vol. XXXIII, Fasciculus V (1950), No. 152, pp. 1183-1194.
Morissette et al., Advanced Drug Delivery Reviews, 2004, 56, pp. 275-300.
Notice of Allowance mailed Jun. 26, 2007, in co-pending U.S. Appl. No. 10/999,999.
Notice of Allowance mailed Mar. 9, 2007, in co-pending U.S. Appl. No. 10/999,999.
Notice of rejection in counterpart Japanese Application No. 2004-348020, mailed Dec. 6, 2005.
Notice of rejection in counterpart Japanese Application No. 2004-348020, mailed Jan. 29, 2008.
Office Action mailed Apr. 14, 2009, in co-pending U.S. Appl. No. 11/812,616.
Office Action mailed Apr. 16, 2009, in co-pending U.S. Appl. No. 11/812,610.
Office Action mailed Apr. 27, 2009, in co-pending U.S. Appl. No. 11/987,451.
Office Action mailed Mar. 2, 2009, in co-pending U.S. Appl. No. 11/898,438.
Office Action mailed Mar. 24, 2009, in co-pending U.S. Appl. No. 11/812,603.
STIC Search Report for U.S. Appl. No. 10/999,999, dated Dec. 13, 2006.
Vippagunta, S.R., "Crystalline Solids," Advanced Drug Delivery Reviews, 2001, 48, pp. 3-26.

* cited by examiner

DYE COMPOSITION OF ACIDIC PH COMPRISING 2,3-DIAMINO-6,7-DIHYDRO-1H,5H-PYRAZOLO[1,2-A]PYRAZOL-1-ONE, A COUPLER, A PARTICULAR SURFACTANT AND AN OXIDIZING AGENT AND PROCESSES AND KITS USING SAID COMPOSITION

This application claims benefit of U.S. Provisional Application No. 60/874,271, filed Dec. 12, 2006, the contents of which are incorporated herein by reference. This application also claims benefit of priority under 35 U.S.C. § 119 to French Patent Application No. FR 0655213, filed Nov. 30, 2006, the contents of which are also incorporated herein by reference.

Disclosed herein are compositions for dyeing keratin fibers, for example, human keratin fibers such as the hair, comprising at least one oxidation base chosen from 2,3-diamino-6,7-dihydro-1H,5H-pyrazolo[1,2-a]pyrazol-1-one and addition salts thereof, at least one coupler, at least one surfactant chosen from oxyalkylenated or glycerolated fatty alcohols, anionic surfactants of sulfate or sulfonate type and amphoteric surfactants of betaine type, and at least one oxidizing agent, wherein the pH of the composition ranges from 5.5 to 7.5.

It is known practice to dye keratin fibers, for example human keratin fibers such as the hair, with dye compositions comprising oxidation dye precursors, such as ortho- or para-phenylenediamines, ortho- or para-aminophenols, and heterocyclic compounds such as diaminopyrazole derivatives, pyrazolo[1,5-a]pyrimidine derivatives, pyrimidine derivatives, pyridine derivatives, indole derivatives and indoline derivatives, which are generally known as oxidation bases. Oxidation dye precursors, or oxidation bases, are colorless or weakly colored compounds that, when combined with oxidizing products, can give rise to dyes or colored compounds via a process of oxidative condensation. Permanent colorations are thus obtained.

It is also known that the shades obtained With these oxidation bases may be varied by combining them with couplers or coloration modifiers, the latter being chosen, for example, from meta-phenylenediamines, meta-aminophenols, meta-hydroxyphenols and certain heterocyclic compounds.

The variety of molecules used as oxidation bases and couplers allows a wide range of colors to be obtained.

The use of standard oxidation bases such as para-aminophenol, ortho-aminophenol and derivatives thereof optionally combined with standard couplers at acidic pH often does not make it possible to obtain shades with tints in red, coppery or mahogany tones that are sufficiently visible on natural or dyed hair and/or are uniform from the roots to the ends.

Thus, disclosed herein are novel compositions for dyeing keratin fibers, which may make it possible to obtain at acidic pH a coloration with tints in red, coppery or mahogany tones that may be particularly visible, strong, chromatic, aesthetic, sparingly selective and/or resistant or very resistant to one or more of the various attacking factors to which the hair may be subjected, such as shampoo, light, sweat and permanent reshaping operations.

Disclosed herein is thus a composition for dyeing keratin fibers, comprising, in at least one suitable dyeing medium:
at least one oxidation base chosen from 2,3-diamino-6,7-dihydro-1H,5H-pyrazolo[1,2-a]pyrazol-1-one of formula (I) below, and addition salts thereof:

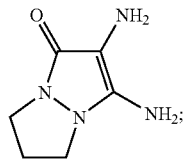

at least one coupler;
at least one surfactant chosen from oxyalkylenated or glycerolated fatty alcohols, anionic surfactants of sulfate or sulfonate type and amphoteric surfactants of betaine type; and
at least one oxidizing agent;
wherein the pH of the composition ranges from 5.5 to 7.5;
with the proviso that when the composition comprises at least one oxyalkylenated or glycerolated fatty alcohol, it is free:
of 3-amino-2-methylamino-6-methoxypyridine;
of fatty-chain cationic polyurethane obtained from the condensation of 1,3-bis(isocyanatomethylcyclohexane)N,N-dimethylethanolamine quaternized with bromodecane N,N-dimethylethanolamine and polyoxyethylene;
of polycondensates of polyethylene glycol comprising 150 or 180 mol of ethylene oxide, decyl alcohol and methylenebis(4-cyclohexyl isocyanate);
of mixtures of cetearyl alcohol polyglycerolated with 2 mol of glycerol and of cetearyl alcohol polyglycerolated with 6 mol of glycerol; and
of hexylene glycol.

The compositions disclosed herein may make it possible to obtain a coloration on keratin fibers with tints in red, coppery or mahogany tones that are sufficiently visible on natural or dyed hair and/or are uniform from the roots to the ends.

Also disclosed herein is a process for dyeing keratin fibers, such as, for example, human keratin fibers such as the hair, using the composition disclosed herein.

Further disclosed herein are dyeing kits comprising, in a first compartment, a dyeing composition comprising at least one oxidation base chosen from 2,3-diamino-6,7-dihydro-1H,5H-pyrazolo[1,2-a]pyrazol-1-one and addition salts thereof, at least one coupler and at least one surfactant chosen from oxyalkylenated or glycerolated fatty alcohols, anionic surfactants of sulfate or sulfonate type and amphoteric surfactants of betaine type, and, in a second compartment, a composition containing at least one oxidizing agent.

Unless otherwise indicated, the limits of the ranges of values that are given in the context of the present invention are included in these ranges.

Oxidation Bases

The at least one oxidation base chosen from 2,3-diamino-6,7-dihydro-1H,5H-pyrazolo[1,2-a]pyrazol-1-one of formula (I) and the addition salts thereof may be present in the composition disclosed herein in an amount, for each if more than one is present, ranging from 0.001% to 10% by weight relative to the total weight of the dye composition, for example ranging from 0.005% to 6%.

Couplers

The at least one coupler of the presently disclosed composition may be chosen from meta-phenylenediamines, meta-aminophenols, meta-diphenols, naphthalene-based couplers and heterocyclic couplers, and the addition salts thereof.

Examples of couplers that may be mentioned include, but are not limited to, 2-methyl-5-aminophenol, 5-N-(β-hydroxyethyl)amino-2-methylphenol, 6-chloro-2-methyl-5- aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the acid-addition salts thereof.

In at least one embodiment, the at least one coupler is chosen from meta-aminophenols. In a further embodiment, the at least one coupler is chosen from meta-aminophenols of formula (II) below, and the addition salts thereof:

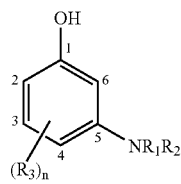

(II)

wherein:

$R_1$ and $R_2$, which may be identical or different, are chosen from hydrogen atoms; alkyl radicals; monohydroxyalkyl radicals; polyhydroxyalkyl radicals; and monoaminoalkyl radicals; or $R_1$ and $R_2$ may form, together with the nitrogen atom to which they are attached, a saturated or unsaturated, 5- to 7-membered cyclic group comprising at least one heteroatom, optionally substituted with at least one radical chosen from carboxyl, carboxamido, hydroxyl, amino, monoalkylamino and dialkylamino radicals, and alkyl radicals optionally substituted with at least one radical chosen from hydroxyl, amino, monoalkylamino and dialkylamino radical;

$R_3$ are chosen, independently of each other, from halogen atoms; alkyl radicals; alkoxy radicals; monohydroxyalkyl radicals; polyhydroxyalkyl radicals; monohydroxyalkoxy radicals; and polyhydroxyalkoxy radicals;

n is an integer ranging from 0 to 3.

As used herein, the term "alkyl radical" means, unless otherwise indicated, linear or branched $C_1$ to $C_{10}$ alkyl radicals, for example $C_1$ to $C_6$, or $C_1$ to $C_4$, alkyl radicals, such as methyl, ethyl, propyl, isopropyl, isobutyl, tert-butyl, pentyl or hexyl radicals.

According to the present disclosure, a "heteroatom" may be chosen from oxygen, nitrogen, sulfur, and phosphorus atoms.

According to the present disclosure, a "halogen atom" may be chosen from chlorine, bromine, iodine and fluorine atoms.

In at least one embodiment, $R_1$ and $R_2$ are chosen from, independently of each other, hydrogen atoms; alkyl radicals, for example methyl or ethyl radicals; and monohydroxyalkyl radicals, for example β-hydroxyethyl or γ-hydroxypropyl radicals; or $R_1$ and $R_2$ form, together with the nitrogen atom to which they are attached, a ring chosen from pyrrolidine, piperidine, homopiperidine, piperazine, homopiperazine and morpholine heterocycles; wherein said ring is optionally substituted with at least one radical chosen from hydroxyl, amino, mono($C_1$-$C_2$)alkylamino, di($C_1$-$C_2$)alkylamino, carboxyl and carboxamido radical, or $C_1$ to $C_4$ alkyl radicals optionally substituted with at least one radical chosen from hydroxyl, amino, mono($C_1$-$C_2$)alkylamino and di($C_1$-$C_2$) alkylamino radicals, wherein said ring, in at least one embodiment, is chosen, for example from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(β-hydroxyethyl)-aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, N-(2-hydroxyethyl)homopiperazine, piperazine, 4-methylpiperazine, 4-ethylpiperazine, 4-(β-hydroxyethyl) piperazine and morpholine, and in a further embodiment, they may form at least one of the following: pyrrolidin-1-yl; piperidin-1-yl; piperazin-1-yl; 4-methylpiperazin-1-yl; 4-ethylpiperazin-1-yl; 4-(β-hydroxyethyl)piperazin-1-yl; or morpholin-4-yl.

In at least one embodiment, $R_3$ is chosen from halogen atoms, alkyl radicals, alkoxy radicals and monohydroxyalkoxy radicals. For example, $R_3$ may be chosen from chlorine atoms, methyl radicals, methoxy radicals and β-hydroxyethyloxy radicals.

According to at least one embodiment, n is chosen from 0, 1 and 2. For example, n may be equal to 1 or 2. In at least one embodiment, when n is equal to 1, $R_3$ may be in position 2 and when n is equal to 2, $R_3$ may be in positions 2 and 4 or in positions 2 and 6.

Examples of substituted meta-aminophenols of formula (II) include, but are not limited to: 5-amino-2-methoxyphenol; 5-amino-2-(β-hydroxyethyloxy)phenol; 5-amino-2-methylphenol; 5-N-(β-hydroxyethyl)amino-2-methylphenol; 5-N-(β-hydroxyethyl)amino-4-methoxy-2-methylphenol; 5-amino-4-methoxy-2-methylphenol; 5-amino-4-chloro-2-methylphenol; 6-chloro-2-methyl-5-aminophenol; 5-amino-2,4-dimethoxyphenol; 5-(γ-hydroxypropylamino)-2-methylphenol; 3-dimethylaminophenol; 2-methyl-5-dimethylaminophenol; 2-ethyl-5-dimethylaminophenol; 2-methoxy-5-dimethylaminophenol; 2-ethoxy-5-dimethylaminophenol; 2-(β-hydroxyethyl)-5-dimethylaminophenol; 3-diethylaminophenol; 2-methyl-5-diethylaminophenol; 2-ethyl-5-diethylaminophenol; 2-methoxy-5-diethylaminophenol; 2-ethoxy-5-diethylaminophenol; 2-(β-hydroxyethyl)-5-diethylaminophenol; 3-di(β-hydroxyethyl)aminophenol; 2-methyl-5-di(β-hydroxyethyl)aminophenol; 2-ethyl-5-di(β-hydroxyethyl)aminophenol; 2-methoxy-5-di(β-hydroxyethyl)aminophenol; 2-ethoxy-5-di(β-hydroxyethyl)aminophenol; 2-(β-hydroxyethyl)-5-di(β-hydroxyethyl)aminophenol; 3-pyrrolidin-1-ylphenol; 2-methyl-5-pyrrolidin-1-ylphenol; 2-ethyl-5-pyrrolidin-1-ylphenol; 2-methoxy-5-pyrrolidin-1-ylphenol; 2-ethoxy-5-pyrrolidin-1-ylphenol; 2-(β-hydroxyethyl)-5-pyrrolidin-1-ylphenol; 3-piperidin-1-ylphenol; 2-methyl-5-piperidin-1-ylphenol; 2-ethyl-5-piperidin-1-ylphenol; 2-methoxy-5-piperidin-1-ylphenol; 2-ethoxy-5-piperidin-1-ylphenol; 2-(β-hydroxyethyl)-5-piperidin-1-ylphenol; 3-piperazin-1-ylphenol;

2-methyl-5-piperazin-1-ylphenol; 2-ethyl-5-piperazin-1-ylphenol; 2-methoxy-5-piperazin-1-ylphenol; 2-ethoxy-5-piperazin-1-ylphenol; 2-(β-hydroxyethyl)-5-piperazin-1-ylphenol; 3-(4-methylpiperazin-1-yl)phenol; 2-methyl-5-(4-methylpiperazin-1-yl)phenol; 2-ethyl-5-(4-methylpiperazin-1-yl)phenol; 2-methoxy-5-(4-methylpiperazin-1-yl)phenol; 2-ethoxy-5-(4-methylpiperazin-1-yl)phenol; 2-(β-hydroxyethyl)-5-(4-methylpiperazin-1-yl)phenol; 3-(4-ethylpiperazin-1-yl)phenol; 2-methyl-5-(4-ethylpiperazin-1-yl)phenol; 2-ethyl-5-(4-ethylpiperazin-1-yl)phenol; 2-methoxy-5-(4-ethylpiperazin-1-yl)phenol; 2-ethoxy-5-(4-ethylpiperazin-1-yl)phenol; 2-(β-hydroxyethyl)-5-(4-ethylpiperazin-1-yl)phenol; 3-(4-(β-hydroxyethyl)piperazin-1-yl)phenol; 2-methyl-5-(4-(β-hydroxyethyl)piperazin-1-yl)phenol; 2-ethyl-5-(4-(β-hydroxyethyl)piperazin-1-yl)phenol; 2-methoxy-5-(4-(β-hydroxyethyl)piperazin-1-yl)phenol; 2-ethoxy-5-(4-(β-hydroxyethyl)piperazin-1-yl)phenol; 2-(β-hydroxyethyl)-5-(4-(β-hydroxyethyl)piperazin-1-yl)phenol; 3-morpholin-4-ylphenol; 2-methyl-5-morpholin-4-ylphenol; 2-ethyl-5-morpholin-4-ylphenol; 2-methoxy-5-morpholin-4-ylphenol; 2-ethoxy-5-morpholin-4-ylphenol; and 2-(β-hydroxyethyl)-5-morpholin-4-ylphenol.

In at least one embodiment, $R_1$ and $R_2$ are chosen from, independently of each other, hydrogen atoms and mono- or polyhydroxyalkyl radicals, for example 5-amino-2-methylphenol and 5-[N-(β-hydroxyethyl)amino]-2-methylphenol.

In another embodiment, the at least one meta-aminophenol is chosen from chlorinated meta-aminophenols. As used herein, the term "chlorinated meta-aminophenol" means a meta-aminophenol comprising in its structure at least one chlorine atom, for example 6-chloro-2-methyl-5-aminophenol.

In the presently disclosed composition, the at least one coupler is present in an amount, for each if there are more than one, ranging from 0.001% to 10% by weight relative to the total weight of the dye composition, for example from 0.005% to 6% by weight.

Surfactants

As disclosed above, the present composition comprises, inter alia, at least one surfactant chosen from oxyalkylenated or glycerolated fatty alcohols, anionic surfactants of sulfate or sulfonate type and amphoteric surfactants of betaine type.

The oxyalkylenated fatty alcohols may be chosen, in at least one embodiment, from the compounds of formula (III) below:

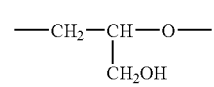

wherein:

R is chosen from saturated or unsaturated, linear or branched radicals containing from 8 to 40 carbon atoms, for example from 8 to 30 carbon atoms, Z is chosen from oxyethylene (i) and/or oxypropylene (ii)$_1$ and (ii)$_2$ radicals having the following respective formulas:

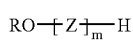

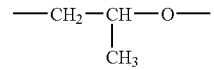

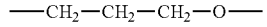

wherein m is the number of ethylene oxide (i) and/or propylene oxide (ii)$_1$ or (ii)$_2$ groups, ranging from 1 to 250, for example from 2 to 100.

The glycerolated fatty alcohols may be chosen, in at least one embodiment, from the compounds of formula (IV) below:

wherein:

R is chosen from saturated or unsaturated, linear or branched radicals comprising from 8 to 40 carbon atoms, for example from 8 to 30 carbon atoms, Z represents a glycerolated radical (iii) of the following formula:

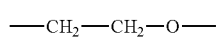

wherein n represents the number of glycerol groups (iii) and ranges from 1 to 30, for example from 1 to 10.

In at least one embodiment, the composition disclosed herein may contain mixtures of the oxyalkylenated and/or glycerolated fatty alcohols.

In a further embodiment, the oxyalkylenated fatty alcohols are chosen from saturated or unsaturated, linear or branched fatty alcohols comprising from 10 to 20 carbon atoms and from 2 to 40 ethylene oxide groups.

Examples of compounds of oxyalkylenated fatty alcohol type, include, but are not limited to, the following marketed products:

MERGITAL LM2 (Cognis) [lauryl alcohol 2 EO];
IFRALAN L12 (Ifrachem) and REWOPAL 12 (Goldschmidt) [lauryl alcohol 12 EO];
EMPILAN KA 2.5/90FL (Albright & Wilson) and MERGITAL BL309 (Cognis) [decyl alcohol 3 EO];
EMPILAN KA 5/90 FL (Albright & Wilson) and MERGITAL BL589 (Cognis) [decyl alcohol 5 EO];
BRIJ 58 (Uniqema) and SIMULSOL 58 (SEPPIC) [cetyl alcohol 20 EO];
EUMULGIN 05 (Cognis) [oleocetyl alcohol 5 EO];
MERGITAL OC30 (Cognis) [oleocetyl alcohol 30 EO];
BRIJ 72 (Uniqema) [stearyl alcohol 2 EO];
BRIJ 76 (Uniqema) [stearyl alcohol 10 EO];
BRIJ 78P (Uniqema) [stearyl alcohol 20 EO];
BRIJ 700 (Uniqema) [stearyl alcohol 100 EO];
EUMULGIN B1 (Cognis) [cetylstearyl alcohol 12 EO];
EUMULGIN L (Cognis) [cetyl alcohol 9 EO and 2 PO];
WITCONOL APM (Goldschmidt) [myristyl alcohol 3 PO].

Examples of compounds of glycerolated fatty alcohol type include, but are not limited to, lauryl alcohol comprising 4 mol of glycerol (INCI name: Polyglyceryl-4 Lauryl Ether), oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, octadecanol comprising 6 mol of glycerol, and lauryl alcohol comprising 1.5 mol of glycerol (INCI name: Glyceryl Lauryl Ether).

In one embodiment, the fatty alcohol may represent a mixture of fatty alcohols, which means that several oxyalkylenated or glycerolated fatty alcohol species may coexist in a commercial product, in the form of a mixture.

According to at least one embodiment, the anionic surfactants of sulfate or sulfonate type are anionic surfactants comprising at least one sulfate function (—$OSO_3H$ or —$OSO_3$—) and/or one sulfonate function (—$SO_3H$ or —$SO_3$—).

Non-limiting examples of anionic surfactants of sulfate or sulfonate type that may be used, alone or as mixtures, in the context of the present disclosure include: salts, such as alkali metal salts, for example of sodium, ammonium salts, amine salts, amino alcohol salts or magnesium salts, of alkyl sulfates, of alkylamido sulfates, of alkyl ether sulfates, of alkylamido ether sulfates, of alkylaryl ether sulfates, of alkyl ether sulfosuccinates, of acyl isethionates, of methyl acyl taurates or of α-olefin sulfonates; the alkyl or acyl radicals of all these various compounds comprising from 8 to 24 carbon atoms, and the aryl radicals comprising at least one phenyl or benzyl group; and mixtures thereof.

In at least one embodiment, the mean number of ethylene oxide or propylene oxide groups may range from 2 to 50, for example from 2 to 10.

The amphoteric surfactant(s) of betaine type may be chosen, in at least one embodiment, from ($C_8$-$C_{20}$)alkylbetaines, sulfobetaines, ($C_8$-$C_{20}$)alkylamido($C_1$-$C_6$)alkylbetaines and ($C_8$-$C_{20}$)alkylamido($C_1$-$C_6$)alkylsulfobetaines.

In another embodiment, the at least one amphoteric surfactant may belong to the group of betaines such as alkylbetaines, for example the cocoylbetaine sold under the name DEHYTON AB 30 as an aqueous solution containing 30% AM by the company Henkel, or alkylamidobetaines, for example cocoamidopropylbetaine such as Tegobetaine® F50 sold by the company Goldschmidt.

In one embodiment the at least one surfactant chosen from oxyalkylenated or glycerolated fatty alcohols, anionic surfactants of sulfate or sulfonate type and amphoteric surfactants of betaine type is present in an amount ranging from 0.05% to 50% by weight relative to the total weight of the composition, for example from 0.5% to 40% by weight, or from 1% to 20% by weight.

Additional Oxidation Bases

In at least one embodiment, the composition of the present invention may comprise at least one additional oxidation base chosen from para-phenylenediamines, bis(phenyl)alkylenediamines, para-aminophenols, bis-para-aminophenols, ortho-aminophenols, ortho-phenylenediamines and heterocyclic bases other than 2,3-diamino-6,7-dihydro-1H,5H-pyrazolo[1,2-a]pyrazol-1-one, and the addition salts thereof.

Examples of para-phenylenediamines include, but are not limited to para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and 6-(4-aminophenylamino)hexan-1-ol, and the addition salts thereof.

In a further embodiment, the para-phenylenediamines are chosen from, for example, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine 2-β-acetylaminoethyloxy-para-phenylenediamine and 6-(4-aminophenylamino)hexan-1-ol, and the addition salts thereof.

Examples of bis(phenyl)alkylenediamines include, but are not limited to N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Examples of para-aminophenols include, but are not limited to para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid-addition salts thereof.

Examples of ortho-aminophenols include, but are not limited to 2-aminophenol, 2-amino-5-methylphenol, 2-amino-6-methylphenol and 5-acetamido-2-aminophenol, and the addition salts thereof.

Examples of heterocyclic bases include, but are not limited to pyridine derivatives, pyrimidine derivatives and pyrazole derivatives.

Examples of pyridine derivatives include, but are not limited to the compounds described in patents GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof.

Examples of other pyridine oxidation bases include, but are not limited to 3-aminopyrazolo[1,5-a]pyridine oxidation bases or the addition salts thereof described, for example, in French patent application FR 2 801 308. By way of example, mention may be made of pyrazolo[1,5-a]pyrid-3-ylamine;

2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol and also the addition salts thereof.

Examples of pyrimidine derivatives include, but are not limited to the compounds described in German patent DE 23 59 399; Japanese patent applications JP 88-169 571 and JP 05 163 124; European patent application EP 0 770 375 and International patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French patent application FR-A-2 750 048, such as pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof and the tautomeric forms thereof, when a tautomeric equilibrium exists.

Examples of pyrazole derivatives include, but are not limited to the compounds described in German patents DE 38 43 892 and DE 41 33 957 and International patent applications WO 94/08969 and WO 94/08970, French patent application FR-A-2 733 749 and German patent application DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

In at least one embodiment, when the composition disclosed herein comprises at least one additional oxidation base, the at least one additional oxidation base is present in an amount, for each additional oxidation base if more than one is present, ranging from 0.001% to 10% by weight relative to the total weight of the dye composition, for example from 0.005% to 6%.

Addition Salts

In at least one embodiment, the addition salts of the oxidation bases and of the couplers that may be used in the context of the present disclosure are chosen, for example, from acid-addition salts, such as the hydrochlorides, hydrobromides, sulfates, citrates, succinates, tartrates, lactates, $(C_1-C_4)$alkylsulfonates, tosylates, benzenesulfonates, phosphates and acetates, and base-addition salts, such as sodium hydroxide, potassium hydroxide, ammonia, amines or alkanolamines.

Oxidizing Agents

In at least one embodiment, the at least one oxidizing agent may be chosen from oxidizing agents conventionally used for the oxidation dyeing of keratin fibers, for example hydrogen peroxide, urea peroxide, alkali metal bromates, persalts such as perborates and persulfates, peracids and oxidase enzymes, such as peroxidases, 2-electron oxidoreductases such as uricases and 4-electron oxygenases, for instance laccases, the oxidase enzymes optionally being in the presence of the cofactors thereof. In a further embodiment, hydrogen peroxide is used as the oxidizing agent.

In at least one embodiment, the at least one oxidizing agent is present in an amount ranging from 0.01% to 30% by weight relative to the total weight of the composition, for example from 0.1% to 20%.

pH

The pH of the dye composition in accordance with the present disclosure ranges from 5.5 to 7.5, for example from 5.7 to 6.9. It may be adjusted to the desired value by means of acidifying or basifying agents usually used in the dyeing of keratin fibers, or alternatively using standard buffer systems.

Examples of acidifying agents that include, but are not limited to inorganic or organic acids, such as hydrochloric acid, orthophosphoric acid, sulfuric acid, carboxylic acids such as acetic acid, tartaric acid, citric acid and lactic acid, and sulfonic acids.

Examples of basifying agents include, but are not limited to aqueous ammonia, alkaline carbonates, alkanolamines such as mono-, di- and triethanolamine and derivatives thereof, sodium hydroxide, potassium hydroxide and the compounds of formula (V) below:

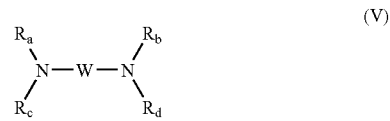

wherein W is a propylene residue that is optionally substituted with a hydroxyl group or a $C_1$ to $C_4$ alkyl radical; $R_a$, $R_b$, $R_c$ and $R_d$, which may be identical or different, are chosen from hydrogen atoms, $C_1$ to $C_4$ alkyl radicals and $C_1$ to $C_4$ hydroxyalkyl radicals.

Dyeing Medium

The medium that is suitable for dyeing, also known as the dye support, is a cosmetic medium that comprises water or a mixture of water and at least one organic solvent to dissolve compounds that are not sufficiently soluble in water. Examples of organic solvents include, but are not limited to: $C_1$ to $C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol; and mixtures thereof.

In at least one embodiment, the solvents are present in an amount ranging from 1% to 40% by weight relative to the total weight of the dye composition, for example from 5% to 30% by weight.

Adjuvants

In at least one embodiment, the dye composition disclosed herein may also comprise various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, for example anionic, cationic, nonionic or amphoteric associative polymeric thickeners, antioxidants, penetrants, sequestrants, fragrances, buffers, dispersants, conditioning agents, for instance silicones, which may be volatile or non-volatile, and modified or unmodified, film-forming agents, ceramides, preserving agents and opacifiers.

In one embodiment, the at least one adjuvant is present in an amount, for each if there are more than one, ranging from 0.01% to 20% by weight relative to the weight of the dye composition.

Needless to say, a person skilled in the art will take care to select this or these optional additional compounds such that the advantageous properties intrinsically associated with the oxidation dye composition in accordance with the disclosure are not, or are not substantially, adversely affected by the addition envisaged.

Form of the Composition

The dye compositions disclosed herein may be in various forms, such as in the form of liquids, creams or gels, or in any other form that is suitable for dyeing keratin fibers, such as human hair.

Dyeing Processes and Kits

The process in accordance with one embodiment of the present disclosure is a process for dyeing keratin fibers wherein the composition disclosed herein is applied to the fibers for a time that is sufficient to develop a desired coloration, after which the fibers are rinsed, optionally washed with shampoo, rinsed again and dried.

In at least one embodiment, the time required to develop the coloration on the keratin fibers ranges from 2 to 60 minutes, for example from 3 to 40 minutes, or from 5 to 30 minutes.

In another embodiment, the process comprises a preliminary step of separately storing, on the one hand, at least one composition (A) comprising, in a suitable dyeing medium, at least one oxidation base chosen from 2,3-diamino-6,7-dihydro-1H,5H-pyrazolo[1,2-a]pyrazol-1-one and addition salts thereof, at least one coupler and at least one surfactant chosen from oxyalkylenated or glycerolated fatty alcohols, anionic surfactants of sulfate or sulfonate type and amphoteric surfactants of betaine type, and, on the other hand, at least one composition (B) comprising, in a suitable dyeing medium, at least one oxidizing agent, and then mixing them together at the time of use before applying this mixture to the keratin fibers.

In at least one embodiment, the compositions (A) and (B) are such that, when their mixture comprises an oxyalkylenated or glycerolated fatty alcohol, it is free:

of 3-amino-2-methylamino-6-methoxypyridine;

of fatty-chain cationic polyurethane obtained from the condensation of 1,3-bis(isocyanatomethylcyclohexane)N,N-dimethylethanolamine quaternized with bromodecane N,N-dimethylethanolamine and polyoxyethylene;

of a polycondensate of polyethylene glycol comprising 150 or 180 mol of ethylene oxide, decyl alcohol and methylenebis(4-cyclohexyl isocyanate);

of mixtures of cetearyl alcohol polyglycerolated with 2 mol of glycerol and of cetearyl alcohol polyglycerolated with 6 mol of glycerol; and of hexylene glycol.

In at least one embodiment, compositions (A) and (B) may also comprise various adjuvants conventionally used in hair dye compositions, including, for example, those previously disclosed herein.

In at least one embodiment, the pH of composition (A) ranges from 3 to 12, for example from 5 to 11. It may be adjusted to the desired value by means of acidifying or basifying agents as disclosed herein, or alternatively by using standard buffer systems.

In at least one embodiment, the pH of composition (B) is such that, after mixing with composition (A), the pH of the resulting composition applied to the keratin fibers ranges from 5.5 to 7.5, for example from 5.6 to 6.9. It may be adjusted to the desired value by means of acidifying or basifying agents as defined above, or alternatively by using standard buffer systems.

Also disclosed herein is a multi-compartment dyeing device or "kit" or any other multi-compartment conditioning system, a first compartment of which comprises composition (A) as disclosed herein and a second compartment of which comprises composition (B) as disclosed herein. These devices may be equipped with a means for applying the desired mixture to the hair, such as the devices described in French patent FR-2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

Example 1

The following composition was prepared:

| | |
|---|---:|
| Sequestrants | 2 g |
| Reducing agents | 0.71 g |
| Ethanolamine | 2.27 g |
| Citric acid | 0.15 g |
| Fumed silica of hydrophobic nature | 1.2 g |
| 2,3-Diamino-6,7-dihydro-1H,5H-pyrazolo[1,2-a]pyrazol-1-one•2 $CH_3$—$SO_3H$ | 1.9 g |
| 4-Amino-2-hydroxytoluene | 0.2 g |
| 6-Chloro-2-methyl-5-aminophenol | 0.8 g |
| para-Aminophenol | 0.1 g |
| Glycol distearate | 2 g |
| Fragrance | 0.95 g |
| Tetramethylhexamethylenediamine/1,3-dichloropropylene polycondensate | 4 g |
| Dimethyldiallylammonium chloride/acrylic acid copolymer (80/20) | 3 g |
| Carbopol 980 | 0.4 g |
| Propylene glycol | 10 g |
| Lauric acid | 3 g |
| Oxyethylenated lauryl alcohol (12 EO) | 7 g |
| Cetylstearyl alcohol | 11.5 g |
| Oxyethylenated decyl alcohol (3 EO) | 10 g |
| Oxyethylenated oleocetyl alcohol (30 EO) | 4 g |
| Ascorbic acid | 0.25 g |
| Water | 34.57 g |

At the time of use, 1 part by weight of the composition described above was mixed with 1 part by weight of a 20-volumes hydrogen peroxide solution whose pH was equal to 2.3. A final pH of 6.8±0.2 was obtained.

The mixture obtained was applied to locks of natural or permanent-waved grey hair containing 90% white hairs. After a leave-on time of 20 minutes at 22° C.±3° C., the locks were rinsed, washed with a standard shampoo, rinsed again and then dried.

The hair coloration was evaluated visually. A shade with a strong coppery tint was obtained.

Example 2

The following composition was prepared:

| | |
|---|---:|
| Sequestrants | 0.2 g |
| Antioxidants | 0.2 g |
| Ethanolamine | 0.2 g |
| Reducing agents | 1 g |
| 2,3-Diamino-6,7-dihydro-1H,5H-pyrazolo[1,2-a]pyrazol-1-one•2 $CH_3$—$SO_3H$ | 1.87 g |
| 4-Amino-2-hydroxytoluene | 1.96 g |
| para-Phenylenediamine | 0.77 g |
| para-Aminophenol | 0.15 g |
| Oleyl alcohol | 6 g |
| Wheat amino acids | 0.5 g |
| Fragrance | 0.3 g |
| Oxyethylenated and oxypropylenated (20/80 EO/PO) poly dimethyl/methylsiloxane (20/5) | 1.5 g |
| Isopropyl alcohol | 10 g |
| Propylene glycol | 7 g |
| Dipropylene glycol monobutyl ether | 5 g |
| Cocoylbetaine (aqueous 30% solution) | 2.5 g |
| Oxyethylenated (10 EO) and oxypropylenated (5 PO) cetyl alcohol hydrogen phosphate | 0.9 g |
| Oxyethylenated decyl alcohol (3 EO) | 9 g |
| Sodium α-olefin sulfonate (aqueous 40% solution) | 22.5 g |
| Lauryl alcohol | 2.5 g |
| Coconut acid monoisopropanolamide | 6.5 g |
| Water | 19.45 g |

At the time of use, 1 part by weight of the composition described above was mixed with 1 part by weight of a 6.7-volumes hydrogen peroxide solution whose pH was equal to 1.8±0.3. A final pH of 6.5±0.3 was obtained.

The mixture obtained was applied to locks of natural or permanent-waved grey hair containing 90% white hairs. After a leave-on time of 20 minutes at 33° C., the locks were rinsed, washed with a standard shampoo, rinsed again and then dried.

The hair coloration was evaluated visually. A red shade was obtained.

Example 3

The following composition was prepared:

| | |
|---|---:|
| Sequestrants | 0.2 g |
| Antioxidants | 0.2 g |
| Ethanolamine | 0.2 g |
| Reducing agents | 1 g |
| 2,3-Diamino-6,7-dihydro-1H,5H-pyrazolo[1,2-a]pyrazol-1-one•2 $CH_3$—$SO_3H$ | 0.9 g |
| 2-Methylresorcinol | 0.2 g |
| 6-Hydroxyindole | 0.7 g |
| 2-Amino-3-hydroxypyridine | 0.35 g |
| Resorcinol | 0.1 g |
| para-Phenylenediamine | 0.5 g |
| 6-Chloro-2-methyl-5-aminophenol | 0.1 g |
| Oleyl alcohol | 6 g |
| Wheat amino acids | 0.5 g |
| Fragrance | 0.3 g |
| Oxyethylenated and oxypropylenated (20/80 EO/PO) poly dimethyl/methylsiloxane (20/5) | 1.5 g |
| Isopropyl alcohol | 10 g |
| Propylene glycol | 7 g |
| Dipropylene glycol monobutyl ether | 5 g |
| Cocoylbetaine (aqueous 30% solution) | 2.5 g |
| Oxyethylenated (10 EO) and oxypropylenated (5 PO) cetyl alcohol hydrogen phosphate | 0.9 g |
| Oxyethylenated decyl alcohol (3 EO) | 9 g |
| Sodium α-olefin sulfonate (aqueous 40% solution) | 22.5 g |
| Lauryl alcohol | 2.5 g |
| Coconut acid monoisopropanolamide | 6.5 g |
| Water | 21.35 g |

At the time of use, 1 part by weight of the composition described above was mixed with 1 part by weight of a 6.7-volumes hydrogen peroxide solution whose pH was equal to 1.8±0.3. A final pH of 6.5±0.3 was obtained.

The mixture obtained was applied to locks of natural or permanent-waved grey hair containing 90% white hairs. After a leave-on time of 20 minutes at 33° C., the locks were rinsed, washed with a standard shampoo, rinsed again and then dried.

The hair coloration was evaluated visually. A mahogany shade was obtained.

What is claimed is:

1. A composition for dyeing keratin fibers, comprising, in a suitable dyeing medium:

at least one oxidation base chosen from 2,3-diamino-6,7-dihydro-1H,5H-pyrazolo[1,2-a]pyrazol-1-one of formula (I) below, and addition salts thereof:

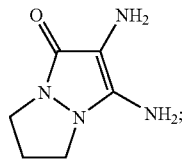

at least one coupler;
at least one surfactant chosen from oxyalkylenated and glycerolated fatty alcohols, anionic surfactants of sulfate or sulfonate type and amphoteric surfactants of betaine type; and
at least one oxidizing agent;
wherein the pH of the composition ranges from 5.5 to 7.5; and with the proviso that when the composition comprises an oxyalkylenated or glycerolated fatty alcohol, it is free:
of 3-amino-2-methylamino-6-methoxypyridine;
of fatty-chain cationic polyurethane obtained from the condensation of 1,3-bis(isocyanatomethylcyclohexane)N,N-dimethylethanolamine quaternized with bromodecane N,N-dimethylethanolamine and polyoxyethylene;
of a polycondensate of polyethylene glycol comprising 150 or 180 mol of ethylene oxide, decyl alcohol and methylenebis(4-cyclohexyl isocyanate);
of mixtures of cetearyl alcohol polyglycerolated with 2 mol of glycerol and of cetearyl alcohol polyglycerolated with 6 mol of glycerol; and
of hexylene glycol.

2. The composition according to claim 1, wherein the at least one oxidation base is present in an amount, for each if more than one are present, ranging from 0.001% to 10% by weight relative to the total weight of the composition.

3. The composition according to claim 1, wherein the at least one coupler is chosen from meta-phenylenediamines, meta-aminophenols, meta-diphenols, naphthalene-based couplers and heterocyclic couplers, and the addition salts thereof.

4. The composition according to claim 3, wherein the at least one coupler is chosen from meta-aminophenols.

5. The composition according to claim 4, wherein at least one meta-aminophenol is chosen from compounds of formula (II) below, and addition salts thereof:

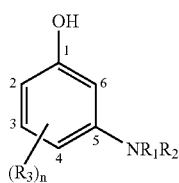

wherein:
$R_1$ and $R_2$, which may be identical or different, are chosen from hydrogen atoms; alkyl radicals; monohydroxyalkyl radicals; polyhydroxyalkyl radicals; and monoaminoalkyl radicals;
$R_1$ and $R_2$ form, together with the nitrogen atom to which they are attached, at least one saturated or unsaturated, 5- to 7-membered cyclic group comprising at least one heteroatom, which is optionally substituted with at least one radical chosen from carboxyl, carboxamido, hydroxyl, amino, monoalkylamino and dialkylamino radicals, and alkyl radicals optionally substituted with at least one radical chosen from hydroxyl, amino, monoalkylamino and dialkylamino radicals;
$R_3$ is chosen from, independently of each other, halogen atoms; alkyl radicals; alkoxy radicals; monohydroxyalkyl radicals; polyhydroxyalkyl radicals; monohydroxyalkoxy radicals; and polyhydroxyalkoxy radicals; and n is an integer ranging from 0 to 3.

6. The composition according to claim 5, wherein $R_1$ and $R_2$ are chosen from, independently of each other, hydrogen atoms and monohydroxyalkyl radicals and polyhydroxyalkyl radicals.

7. The composition according to claim 1, wherein the at least one coupler is chosen from chlorinated meta-aminophenols.

8. The composition according to claim 1, wherein the at least one coupler is present in an amount, for each if more than one is present, ranging from 0.001% to 10% by weight relative to the total weight of the composition.

9. The composition according to claim 1, wherein the oxyalkylenated fatty alcohol is linear or branched, and saturated or unsaturated, and comprises from 8 to 40 carbon atoms and from 1 to 250 ethylene oxide and/or propylene oxide groups.

10. The composition according to claim 9, wherein the oxyalkylenated fatty alcohol is linear or branched, and saturated or unsaturated, and comprises from 10 to 20 carbon atoms and from 2 to 40 ethylene oxide groups.

11. The composition according to claim 1, wherein the glycerolated fatty alcohol is linear or branched, and saturated or unsaturated, and comprises from 8 to 40 carbon atoms and from 1 to 30 glycerol groups.

12. The composition according to claim 1, wherein the at least one anionic surfactant of sulfate or sulfonate type is chosen from the salts of alkyl sulfates, of alkylamido sulfates, of alkyl ether sulfates, of alkylamido ether sulfates, of alkylaryl ether sulfates, of alkyl ether sulfosuccinates, of acyl isethionates, of methyl acyl taurates or of α-olefin sulfonates; the alkyl or acyl radical of all these compounds comprising from 8 to 24 carbon atoms, and the aryl radicals comprising phenyl or benzyl groups; wherein the mean number of ethylene oxide or propylene oxide groups ranges from 2 to 50.

13. The composition according to claim 1, wherein at least one amphoteric surfactant of betaine type is chosen from $(C_8-C_{20})$alkylbetaines, sulfobetaines, $(C_8-C_{20})$alkylamido$(C_1-C_6)$alkylbetaines and $(C_8-C_{20})$alkylamido$(C_1-C_6)$alkylsulfobetaines.

14. The composition according to claim 1, wherein the at least one surfactant is present in an amount ranging from 0.05% to 50% by weight relative to the total weight of the composition.

15. The composition according to claim 1, comprising at least one additional oxidation base chosen from para-phenylenediamines, bis(phenyl)alkylenediamines, para-aminophenols, bis-para-aminophenols, ortho-aminophenols, ortho-phenylenediamines and heterocyclic bases other than 2,3-diamino-6,7-dihydro-1H,5H-pyrazolo[1,2-a]pyrazol-1-one, and addition salts thereof.

16. The composition according to claim 1, wherein the at least one oxidizing agent is chosen from hydrogen peroxide, urea peroxide, alkali metal bromates, persalts, peracids and oxidase enzymes.

17. The composition according to claim 1, wherein the oxidizing agent is present in an amount ranging from 0.01% to 30% by weight relative to the total weight of the composition.

18. A process for dyeing keratin fibers, comprising
applying to said keratin fibers, for a time sufficient to develop a desired coloration, a composition comprising, in a suitable dyeing medium:
at least one oxidation base chosen from 2,3-diamino-6,7-dihydro-1H,5H-pyrazolo[1,2-a]pyrazol-1-one of formula (I) below, and addition salts thereof:

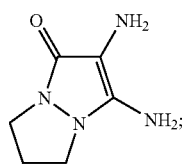

at least one coupler;
at least one surfactant chosen from oxyalkylenated or glycerolated fatty alcohols, anionic surfactants of sulfate or sulfonate type and amphoteric surfactants of betaine type; and
at least one oxidizing agent;
wherein the pH of the composition ranges from 5.5 to 7.5; and with the proviso that when the composition comprises an oxyalkylenated or glycerolated fatty alcohol, it is free of 3-amino-2-methylamino-6-methoxypyridine;
of fatty-chain cationic polyurethane obtained from the condensation of 1,3-bis (isocyanatomethylcyclohexane)N,N-dimethylethanolamine quaternized with bromodecane N,N-dimethylethanolamine and polyoxyethylene;
of a polycondensate of polyethylene glycol comprising 150 or 180 mol of ethylene oxide, decyl alcohol and methylenebis(4-cyclohexyl isocyanate);
of mixtures of cetearyl alcohol polyglycerolated with 2 mol of glycerol and of cetearyl alcohol polyglycerolated with 6 mol of glycerol; and
of hexylene glycol
rinsing said fibers,
optionally washing said fibers with shampoo, and rinsing again, and
drying said fibers.

19. A process for dyeing keratin fibers, said process comprising
separately storing
a composition (A) comprising, in a suitable dyeing medium, at least one oxidation base chosen from 2,3-diamino-6,7-dihydro-1H,5H-pyrazolo[1,2-a]pyrazol-1-one and addition salts thereof, at least one coupler and at least one surfactant chosen from oxyalkylenated or glycerolated fatty alcohols, anionic surfactants of sulfate or sulfonate type and amphoteric surfactants of betaine type, and
a composition (B) comprising, in a suitable dyeing medium, at least one oxidizing agent,
mixing said composition (A) and said composition (B) together at the time of use to form a mixture, wherein when said mixture comprises, from composition (A), an oxyalkylenated or glycerolated fatty alcohol, it is free of 3-amino-2-methylamino-6-methoxypyridine;
of fatty-chain cationic polyurethane obtained from the condensation of 1,3-bis(isocyanatomethylcyclohexane)N,N-dimethylethanolamine quaternized with bromodecane N,N-dimethylethanolamine and polyoxyethylene;
of a polycondensate of polyethylene glycol comprising 150 or 180 mol of ethylene oxide, decyl alcohol and methylenebis(4-cyclohexyl isocyanate);
of mixtures of cetearyl alcohol polyglycerolated with 2 mol of glycerol and of cetearyl alcohol polyglycerolated with 6 mol of glycerol; and
of hexylene glycol,
applying said mixture to said keratin fibers, for a time sufficient to develop a desired coloration,
rinsing said fibers,
optionally washing said fibers with shampoo, and rinsing again, and
drying said fibers.

20. A multi-compartment device, in which a first compartment contains a composition (A), comprising, in a suitable dyeing medium, at least one oxidation base chosen from 2,3-diamino-6,7-dihydro-1H,5H-pyrazolo[1,2-a]pyrazol-1-one and addition salts thereof, at least one coupler and at least one surfactant chosen from oxyalkylenated or glycerolated fatty alcohols, anionic surfactants of sulfate or sulfonate type and amphoteric surfactants of betaine type, and a second compartment contains a composition (B), comprising at least one oxidizing agent in a suitable dyeing medium.

* * * * *